United States Patent
Wang et al.

(10) Patent No.: US 11,576,387 B2
(45) Date of Patent: Feb. 14, 2023

(54) METHOD FOR THE PREPARATION OF BREAD BY COMPOUNDING NATURAL YEAST

(71) Applicant: Jiangnan University, Wuxi (CN)

(72) Inventors: Li Wang, Wuxi (CN); Yafang Yu, Wuxi (CN); Juan Sun, Wuxi (CN); Haifeng Qian, Wuxi (CN); Yan Li, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 547 days.

(21) Appl. No.: 16/531,183

(22) Filed: Aug. 5, 2019

(65) Prior Publication Data

US 2019/0364913 A1    Dec. 5, 2019

Related U.S. Application Data (63) Continuation of application No. PCT/CN2018/121677, filed on Dec. 18, 2018.

(30) Foreign Application Priority Data

Feb. 12, 2018 (CN) .......................... 201810145938.0

(51) Int. Cl.
  *A21D 8/04* (2006.01)
  *C12N 1/18* (2006.01)
  *C12N 1/20* (2006.01)

(52) U.S. Cl.
  CPC ............. *A21D 8/045* (2013.01); *A21D 8/047* (2013.01); *C12N 1/18* (2013.01); *C12N 1/20* (2013.01)

(58) Field of Classification Search
  CPC .............................. A21D 8/045; A21D 8/047
  See application file for complete search history.

(56) References Cited

U.S. PATENT DOCUMENTS

| | | | | |
|---|---|---|---|---|
| 2,023,500 A | * | 12/1935 | Wogerbauer | A21D 8/045 426/62 |
| 5,997,914 A | * | 12/1999 | Shimura | A21D 8/047 426/549 |
| 2011/0217368 A1 | * | 9/2011 | Prakash | A61K 35/747 435/253.4 |

FOREIGN PATENT DOCUMENTS

| CN | 106414710 A | 2/2017 |
|---|---|---|
| CN | 107347963 A | 11/2017 |
| CN | 108102985 A | 6/2018 |

OTHER PUBLICATIONS

Park CN 107208039 2017 (ip.com translation) (Year: 2017).*

(Continued)

*Primary Examiner* — Felicia C Turner
(74) *Attorney, Agent, or Firm* — IPro, PLLC; Na Xu (57) ABSTRACT

The present invention discloses a method for preparing bread by fermentation with compounded sourdough, and belongs to the technical field of food. The method compounds saccharomycetes and lactic acid bacteria to prepare the compounded sourdough. Compared with spontaneous sourdough, the fermentation performance is similar, the quality is stable, the culture period is shortened, and the compounded sourdough can be used to replace the spontaneous sourdough to prepare bread by fermentation. Moreover, the nutritional value of the compounded sourdough bread is much higher than that of the commercial yeast bread using only a single type of yeast, both in terms of the total content of free amino acids and the content of essential amino acids. The compounded sourdough provided by the present invention has extremely high industrial application value.

8 Claims, 7 Drawing Sheets

(56) References Cited

OTHER PUBLICATIONS

Yokohama et al. CN 1886055 Dec. 2006 (ip.com translation) (Year: 2006).*
Zhouping et al. CN 106962741 2017(ip.com translation) (Year: 2017).*

* cited by examiner

METHOD FOR THE PREPARATION OF BREAD BY COMPOUNDING NATURAL YEAST

TECHNICAL FIELD

The disclosure herein relates to a method for preparing bread by fermentation with compounded sourdough (natural yeast), and belongs to the technical field of food.

BACKGROUND

At present, more and more people eat bread as their daily staple food, and the consumption of bread in many countries around the world is increasing year by year. Bread is food made from wheat flour, yeast, table salt and water as main raw materials added with an appropriate amount of auxiliary materials by processes of dough preparation, fermentation, shaping, proofing, baking, etc., and is rich in nutrients, easy to digest and absorb, convenient to eat and easy to store. With economic development and changes in consumption concepts, more and more modern people prefer safe and healthy foods without addition. As one of the main raw materials for bread making, yeast has also attracted the attention of the masses of consumers.

Sourdough (natural yeast) fermentation, despite an ancient bio-fermentation technology, can be combined with the modern technology to produce foods that are preservative-free and more beneficial to the health of the intestines. However, due to the long incubation time, complex matrix, and cockamamie culture process, spontaneous sourdough is easy to be contaminated during back-slopping process, and the flavor of the final product is unstable. So, this method is limited to be used in family or handicraft workshops and difficult to be used for industrial production.

SUMMARY

The present invention discloses a compounded sourdough (natural yeast) which can stabilize a bread fermentation process and product flavor, and lay a good foundation for industrial production.

The compounded sourdough is composed of *Saccharomyces cerevisiae*, *Lactobacillus brevis*, *Lactobacillus reuteri* and *Lactobacillus plantarum*, wherein the proportions of the microorganisms are:

L. brevis, 4 parts,
L. reuteri, 4 parts,
L. plantarum, 4 parts,
S. cerevisiae, 1 part.

The present invention also discloses a method for preparing the compounded sourdough, comprising:

(1) Lactic acid bacteria are inoculated into an MRS or SDB medium at an inoculum amount of 1-3% and expanded and cultured at 26-30° C. (26-30° C. for *Lactobacillus brevis*) or 35-39° C. (35-39° C. for *Lactobacillus reuteri* and *Lactobacillus plantarum*) for 8-14 h, the cells in a growth index period are collected and centrifuged at 3500-5000 rpm for 10-20 minutes, the supernatant is removed, the cells are washed twice with 5-50 times of sterile water by volume and centrifuged, and the supernatant is removed; the *L. brevis*, *L. reuteri* and *L. plantarum* are cultured respectively by the above method;

(2) *Saccharomycetes* is inoculated into a YPD medium at an inoculum amount of 1-3% and expanded and cultured at 26-30° C. for 8-14 h, the cells in the growth index period are collected and centrifuged at 3500-5000 rpm for 10-20 minutes, the supernatant is removed, the cells are washed twice with 5-50 times of sterile water by volume and centrifuged, and the supernatant is removed;

(3) The cells of the *S. cerevisiae*, *L. brevis*, *L. reuteri* and *L. plantarum* are respectively resuspended with 10-50 times of sterile water by volume, the concentration of the bacterial solutions is measured by turbidimetry, and the concentration of each bacterial solution is $10^8$-$10^{10}$ cells/mL; and (4) The resuspended bacterial solutions are compounded in a certain ratio, the volume ratio of the *L. brevis* to the *L. reuteri* to the *L. plantarum* to the *S. cerevisiae* is 4:4:4:1, and the compounded mixed bacterial solution is inoculated into dough at an inoculum amount of $10^7$-$10^9$ viable cells in the compounded bacterial agent per gram of dough, and cultured at 20-28° C. for 8-15 h to obtain the compounded sourdough.

The present invention also provides a method for preparing bread by using the compounded sourdough, comprising:

(1) 20-25 parts of high-gluten flour, 9-14 parts of the compounded sourdough, 1.2-1.5 parts of milk, 0.9-1.2 parts of organic granulated sugar, 0.3-0.5 part of salt, 0.8-1 part of butter, and 8-13 parts of water of 20-25° C. are mixed and stirred to form dough of 20-25° C.;

(2) the dough is fermented at room temperature of 18-25° C. for 1.5-4 h;

(3) shaping: the bread dough is divided according to 50-80 g/part and shaped;

(4) dough proofing: the shaped dough is proofed at a temperature of 28-38° C. and a relative humidity of 70-85% for 1-3 h; and (5) baking: the proofed dough is baked in an oven to obtain bread, wherein the upper baking temperature is 190-220° C., the lower baking temperature is 170-190° C., and the baking time is 25-30 minutes.

Advantages and Effects of the Present Invention (1) The method compounds saccharomycetes and lactic acid bacteria to prepare the compounded sourdough. Compared with the spontaneous sourdough, the leavening properties is similar, the quality is stable, the culture period is shortened, and the compounded sourdough can be used to replace the spontaneous sourdough to prepare bread by fermentation.

(2) The compounded sourdough bread prepared by the present invention has large specific volume, soft and delicate texture, high nutritional value, long shelf life, and similar quality to the spontaneous sourdough bread. Moreover, the nutritional value of the compounded sourdough bread is much higher than that of the commercial yeast bread using only a single type of yeast, both in terms of the total content of free amino acids and the content of essential amino acids.

DETAILED DESCRIPTION

Preparation method of media:

A YPD medium (for *Saccharomyces cerevisiae*) is prepared from 1% of yeast extract, 2% of peptone and 2% of glucose by the following steps: uniformly mixing all components, filling the mixture into a container, sealing the container, and carrying out sterilizing at 115° C. for 20-30 minutes.

An MRS (for Lactic acid bacteria) medium is prepared from 1% of peptone, 1% of beef extract, 0.5% of yeast extract, 0.57% of sodium citrate, 0.262% of dipotassium hydrogen phosphate, 5% of sodium acetate, 2% of glucose, 0.058% of magnesium sulfate heptahydrate, 0.019% of manganese sulfate monohydrate and 0.1% Tween-80 by the following steps: uniformly mixing the components except the Tween-80, the magnesium sulfate heptahydrate, the manganese sulfate monohydrate and the glucose, adjusting the pH to 6.2-6.4, adding the rest components, carrying out uniform mixing, filling the mixture into a container, sealing the container, and carrying out sterilizing at 121° C. for 15-20 minutes.

An SDB (for Lactic acid bacteria) medium is prepared from 2% of maltose, 0.3% of yeast extract, 0.5-1.5% of fresh yeast extractive, 0.03% of Tween-80 and 0.6% of peptone by the following steps: uniformly mixing all components, filling the mixture in a container, sealing the container, and carrying out sterilizing at 121° C. for 30 minutes.

EXAMPLE 1

Preparation of Spontaneous Sourdough Solution and Spontaneous Sourdough

1. Culture of a fruit spontaneous sourdough solution: grapes are thoroughly cleaned with clear water and drained, 200 g of the grapes are taken into a sterile seal bottle, 500 g of sterile water and 40 g of granulated sugar are added, the mixture is stirred uniformly, the seal bottle is sealed and placed at room temperature, the mixture is fermented for 8 days, the bottle cap is opened once a day and the mixture is stirred with sterile chopsticks, and until a large amount of bubbles appear and scent of wine is sent out, the mixture is filtered to obtain the grape sourdough solution.

2. Culture of fruit spontaneous sourdough: on the first day, 300 g of the grape sourdough solution and 300 g of wheat flour are uniformly mixed and placed at a temperature of 18-25° C. and a humidity of 40%-85% for 24 h; on the next day, 300 g of the grape sourdough paste prepared the day before, 300 g of the grape sourdough solution and 300 g of wheat flour are uniformly mixed and placed at a temperature of 18-25° C. and a humidity of 40%-85% for 24 h; on the third day, 300 g of the grape sourdough paste prepared on the second day, 300 g of the grape sourdough solution and 300 g of wheat flour are uniformly mixed and placed at a temperature of 18-23° C. and a humidity of 40%-70% for 6 h, and until a large amount of bubbles appear and scent of wine is sent out, the grape sourdough are obtained.

EXAMPLE 2

Preparation of Compounded Sourdough

1. *S. cerevisiae*, *L. brevis*, *L. reuteri* and *L. plantarum* are inoculated into corresponding media (saccharomycetes is inoculated in YPD, and lactic acid bacteria are inoculated in MRS) at an inoculum amount of 1-3% at 26-30° C. (26-30° C. for *S. cerevisiae* and *L. brevis*) or 35-39° C. (35-39° C. for *L. reuteri* and *L. plantarum*) and expanded and cultured for 8-14 h, the cells in the growth index period are collected and centrifuged at 3500-5000 rpm for 10-20 minutes, the supernatant is removed, the cells are washed twice with 5-50 times of sterile water by volume and centrifuged, and the supernatant is removed.

2. The cells are resuspended with 10-50 times of sterile water by volume, the concentration of the bacterial solutions is measured by turbidimetry, and the concentration of each bacterial solution is $10^8$-$10^{10}$ cells/mL.

3. The resuspended bacterial solutions are compounded in different ratios (volume ratio), the compounded bacterial resuspended bacterial solutions are inoculated into dough at an inoculum amount of $10^7$-$10^9$ viable cells in the compound combination per gram of dough, and cultured at 20-28° C. for 8-15 h to obtain the compounded sourdough with different compounding ratios as shown in Table 1.

TABLE 1

| Different combinations of 4 kinds of strains | |
| --- | --- |
| Combination | L. brevis:L. reuteri:L. plantarum:S. cerevisiae |
| Compound 1 | 12:0:0:1 |
| Compound 2 | 0:12:0:1 |
| Compound 3 | 0:0:12:1 |
| Compound 4 | 6:6:0:1 |
| Compound 5 | 6:0:6:1 |
| Compound 6 | 0:6:6:1 |
| Compound 7 | 4:4:4:1 |
| Compound 8 | 3:6:3:1 |
| Compound 9 | 6:3:3:1 |
| Compound 10 | 3:3:6:1 |
| Compound 11 | 2:6:4:1 |
| Compound 12 | 4:6:2:1 |

EXAMPLE 3

Preparation of Bread 1. 20-25 parts of high-gluten flour, 9-14 parts of the compounded sourdough prepared according to a formula in Table 1 as in Example 2, 1.2-1.5 parts of milk, 0.9-1.2 parts of organic granulated sugar, 0.3-0.5 part of salt, 0.8-1 part of butter, and 8-13 parts of water of 20-25° C. are mixed and stirred to form dough of 20-25° C.;

2. the dough is fermented at room temperature of 18-25° C. for 1.5-4 h;

3. shaping: the bread dough is divided according to 50-80 g/part and shaped;

4. dough proofing: the shaped dough is proofed at a temperature of 28-38° C. and a relative humidity of 70-85% for 1-3 h;

5. baking: the proofed dough is baked in an oven to obtain bread, wherein the upper baking temperature is 180-220° C., the lower baking temperature is 170-190° C., and the baking time is 25-30 minutes.

The effects of different compounding ratios on bread quality are compared, and the results are shown in Table 2.

TABLE 2

Effects of different compounding ratios on bread quality

| Combination | Specific volume (mL/g) | hardness (g) | Sensory score (point) | Free amino acid content (mg/100 g) |
|---|---|---|---|---|
| Compound 1 | 3.99 ± 0.02$^a$ | 588.18 ± 17.33$^d$ | 7.22 ± 0.07$^a$ | 122.3751 ± 4.5512$^a$ |
| Compound 2 | 4.13 ± 0.03$^b$ | 524.25 ± 19.12$^{bc}$ | 7.84 ± 0.04$^c$ | 137.1531 ± 8.2714$^b$ |
| Compound 3 | 4.05 ± 0.03$^a$ | 562.73 ± 16.27$^{cd}$ | 7.55 ± 0.06$^b$ | 136.3617 ± 1.5142$^b$ |
| Compound 4 | 4.09 ± 0.01$^a$ | 547.84 ± 15.66$^c$ | 7.62 ± 0.03$^b$ | 128.8326 ± 8.3141$^{ab}$ |
| Compound 5 | 4.02 ± 0.04$^a$ | 578.19 ± 10.93$^{cd}$ | 7.45 ± 0.04$^b$ | 127.5491 ± 7.5563$^{ab}$ |
| Compound 6 | 4.15 ± 0.02$^b$ | 515.16 ± 15.55$^b$ | 7.93 ± 0.05$^c$ | 140.4382 ± 3.9647$^{bc}$ |
| Compound 7 | 4.31 ± 0.04$^c$ | 467.00 ± 14.01$^a$ | 8.17 ± 0.07$^{cd}$ | 150.5137 ± 5.5142$^c$ |
| Compound 8 | 4.21 ± 0.01$^b$ | 481.63 ± 11.63$^{ab}$ | 8.08 ± 0.06$^c$ | 147.3857 ± 4.7319$^c$ |
| Compound 9 | 4.15 ± 0.05$^b$ | 518.27 ± 17.23$^{bc}$ | 7.89 ± 0.01$^c$ | 139.6115 ± 5.2461$^b$ |
| Compound 10 | 4.17 ± 0.04$^b$ | 504.99 ± 15.62$^b$ | 8.00 ± 0.04$^c$ | 145.3712 ± 4.9986$^{bc}$ |
| Compound 11 | 4.33 ± 0.05$^c$ | 462.32 ± 9.01$^a$ | 8.00 ± 0.07$^c$ | 142.1853 ± 3.2341$^{bc}$ |
| Compound 12 | 4.18 ± 0.04$^b$ | 501.21 ± 15.88$^b$ | 8.05 ± 0.08$^c$ | 144.3218 ± 2.1152$^{bc}$ |

From Table 2, difference in the compounding ratio has an effect on the bread quality. The combinations of compound 7 and compound 11 have a larger specific volume of bread and softer texture. However, according to the sensory score of the bread, the sensory evaluation of the compound 11 combination is lower, and the sensory score of the compound 7 combination is the highest. In terms of the nutritional value of bread, the compound 7 has the highest free amino acid content. By comprehensive consideration, it is determined that the compound 7 has the optimal compounding ratio, i.e., L. brevis:L. reuteri:L. plantarum:S. cerevisiae=4:4:4:1, and the ratio is used as the compounding ratio of the compounded sourdough.

EXAMPLE 4

Preparation of Bread by Using Commercial Yeast, Spontaneous Sourdough Prepared in Example 1, and Compounded Sourdough Consistent with the Present Invention Respectively Compounding is carried out according to the compound combination 7 obtained in Example 3, and the compounded bacterial solution is inoculated into dough at an inoculum amount of $10^7$-$10^9$ viable cells in the compound combination per gram of dough, and cultured at 20-28° C. for 8-15 h to obtain the compounded sourdough.

Referring to the method for preparing bread in Example 3, bread is prepared by using commercial yeast, the spontaneous sourdough prepared in Example 1, and the compounded sourdough corresponding to the compound 7 in Example 3 respectively. The quality of the obtained bread is compared.

TABLE 3

Fermentation performance of different sourdough

| | Commercial yeast | Spontaneous sourdough prepared in Example 1 | Compounded sourdough |
|---|---|---|---|
| maximum dough height (mm) | 72.2 ± 0.53$^b$ | 63.9 ± 0.57$^a$ | 64.3 ± 0.88$^a$ |
| Total volume (mL) | 1467 ± 13.88$^b$ | 1133 ± 11.69$^a$ | 1156 ± 16.21$^a$ |
| Lost $CO_2$ volume (mL) | 309 ± 5.57$^b$ | 139 ± 6.26$^a$ | 152 ± 7.90$^a$ |
| Retention Volume (mL) | 1158 ± 8.31$^b$ | 994 ± 5.43$^a$ | 1004 ± 8.31$^a$ |
| Retention coeff (%) | 78.9 ± 0.60$^a$ | 87.7 ± 0.46$^b$ | 86.9 ± 0.51$^b$ |

Table 3 shows the results of comparing the fermentation performance of different yeasts by F3 Rheofermentometer, wherein the spontaneous sourdough is prepared in Example 1, and the compounded sourdough is the sourdough prepared according to the compound 7 combination in Table 2 above. As can be seen from Table 3, the total volume of the commercial yeast is significantly higher than that of the spontaneous sourdough and the compounded sourdough. However, the retention coeff of the commercial yeast is not as good as that of the compounded sourdough prepared in the present example, so that the specific volume of the compounded sourdough bread is larger than that of the commercial yeast bread. The fermentation properties of the compounded sourdough is similar to that of the spontaneous sourdough, indicating that the compounded sourdough can replace the spontaneous sourdough for bread preparation.

TABLE 4

Quality of bread made with different sourdough

|  | Specific volume (mL/g) | Hardness (g) | Sensory score (point) | Shelf life (d) |
|---|---|---|---|---|
| Commercial yeast bread | 3.96 ± 0.05$^a$ | 614.41 ± 18.43$^b$ | 7.37 ± 0.08$^a$ | 7.2 ± 0.45$^a$ |
| Spontaneous sourdough bread | 4.42 ± 0.05$^c$ | 448.21 ± 13.45$^a$ | 8.28 ± 0.07$^b$ | 10.6 ± 0.55$^b$ |
| Compounded sourdough bread | 4.31 ± 0.04$^b$ | 467.00 ± 14.01$^a$ | 8.17 ± 0.07$^b$ | 9.8 ± 0.45$^b$ |

TABLE 5

Free amino acid content of bread made with different sourdough

|  | Essential amino acid content (mg/100 g) | Total free amino acid content (mg/100 g) |
|---|---|---|
| Commercial yeast bread | 10.9824 ± 0.7487$^a$ | 91.9369 ± 4.2389$^a$ |
| Spontaneous sourdough bread | 24.2208 ± 1.1439$^c$ | 162.7786 ± 6.2231$^b$ |
| Compounded sourdough bread | 19.5862 ± 0.8136$^b$ | 150.5137 ± 5.5142$^b$ |

As can be seen from Table 4 and FIG. 1, the bread prepared by fermentation with the compounded sourdough consistent with the present invention has soft texture, high nutritional value and long shelf life, and can achieve similar properties to spontaneous sourdough bread in terms of specific volume, texture, sensory evaluation and shelf life. The specific volume of the compounded sourdough bread consistent with the present invention is 0.35 more than that of the commercial yeast bread, the hardness is reduced by 24.0%, and the sensory score is 1.1 times that of the commercial yeast bread. As the storage time increases, the increase rate of hardness of the compounded sourdough bread is significantly slower than that of the commercial yeast bread.

Figure 1A:
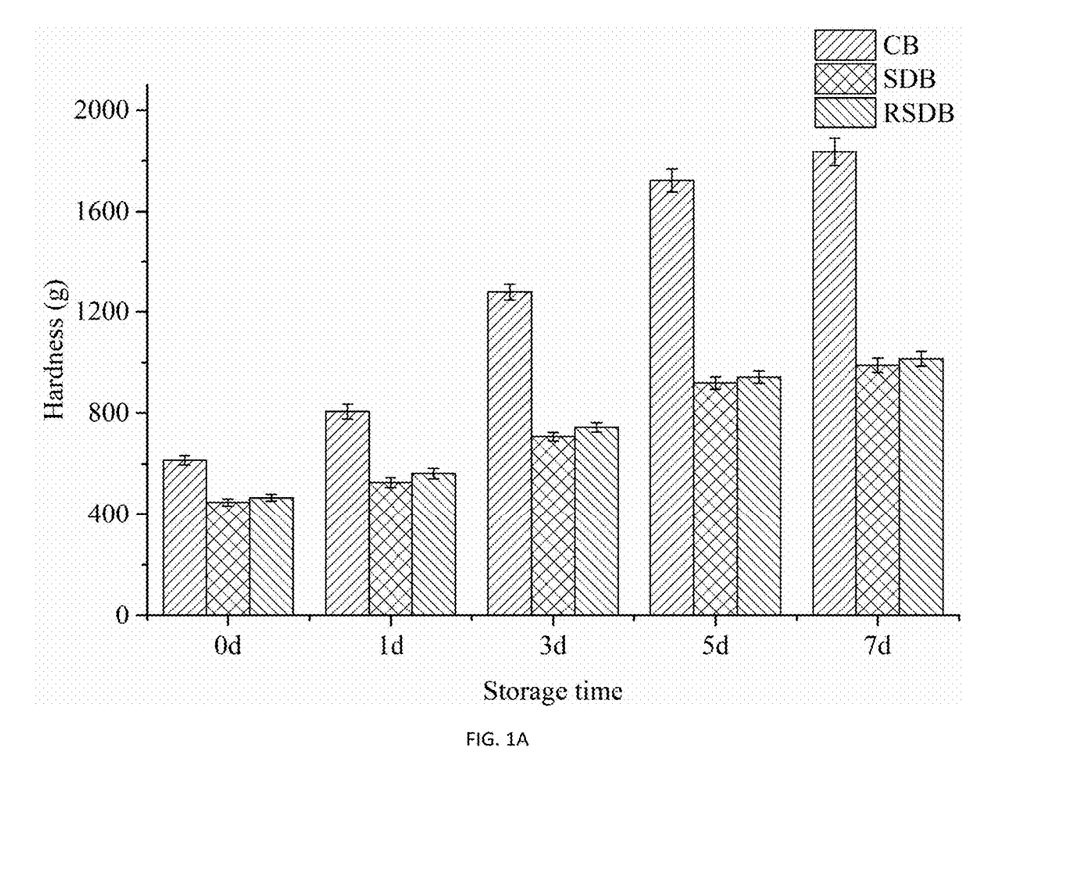
FIG. 1A shows Hardness of bread made with different yeasts during storage (CB: commercial yeast bread, SDB: spontaneous sourdough bread, RSDB: compounded sourdough bread).
Figure 1B:
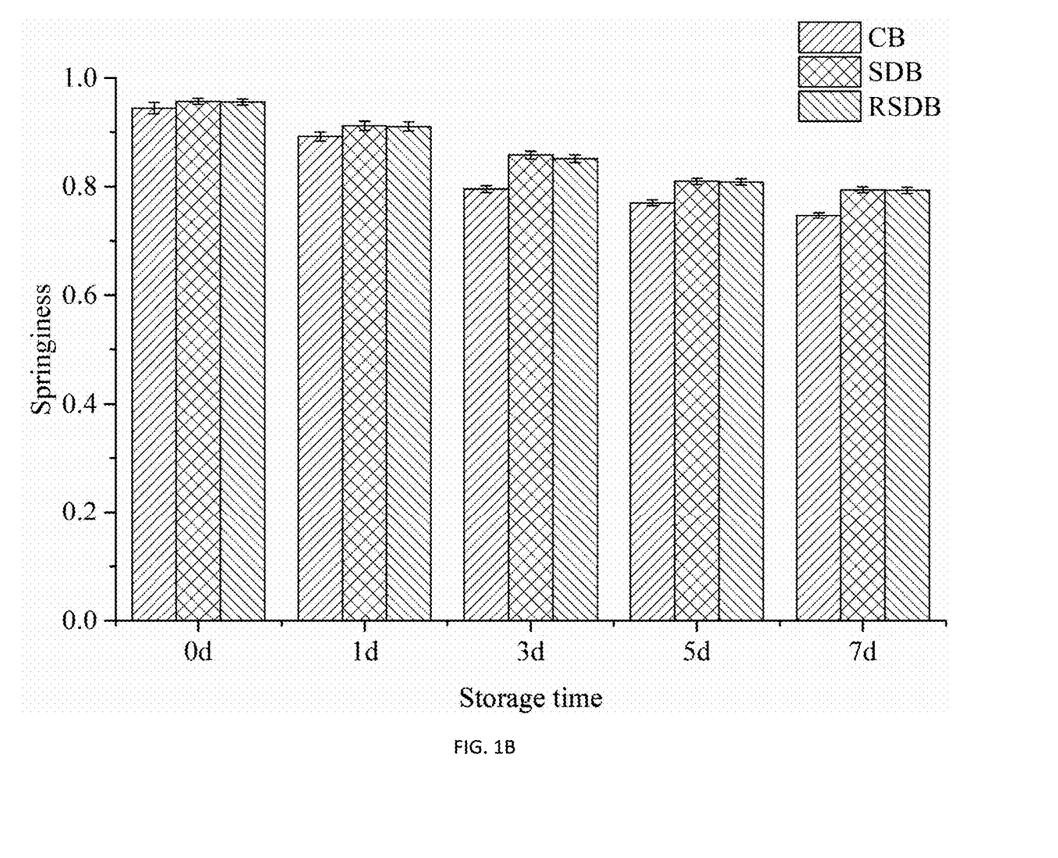
FIG. 1B shows Springiness of bread made with different yeasts during storage (CB: commercial yeast bread, SDB: spontaneous sourdough bread, RSDB: compounded sourdough bread).
Figure 1C:
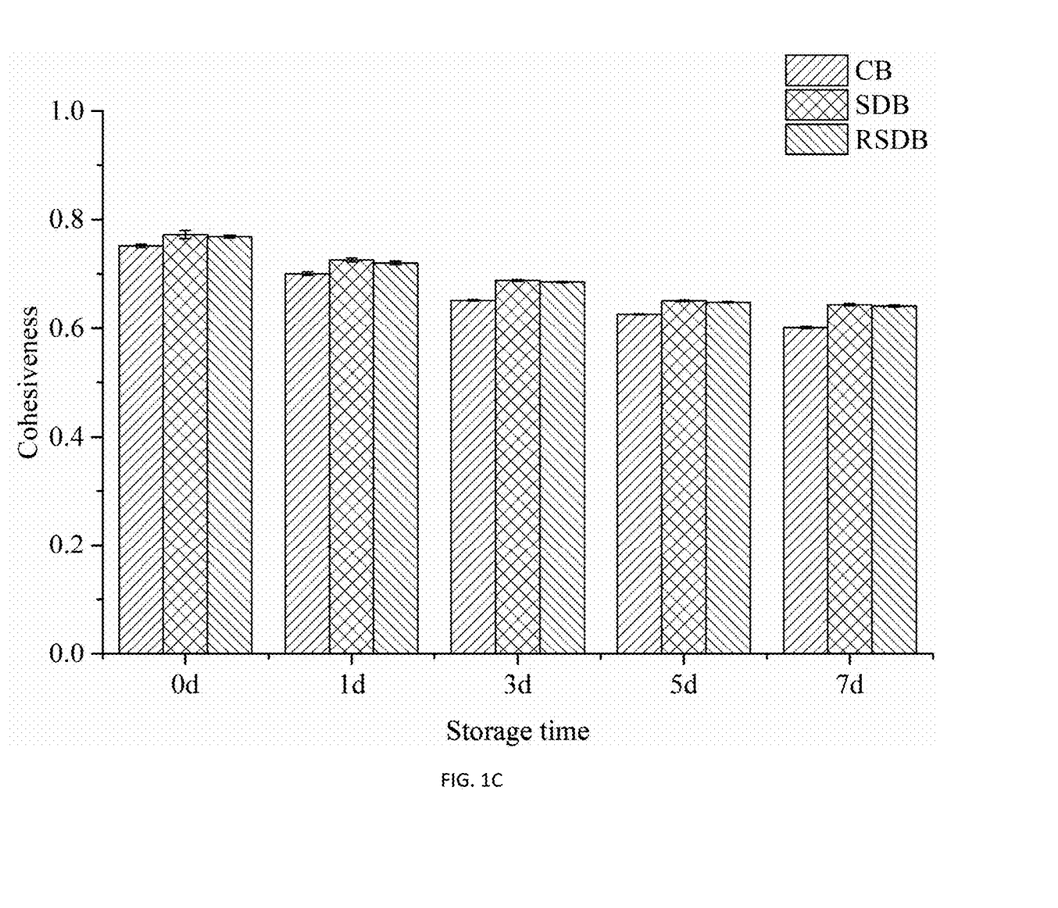
FIG. 1C shows Cohesiveness of bread made with different yeasts during storage (CB: commercial yeast bread, SDB: spontaneous sourdough bread, RSDB: compounded sourdough bread).
Figure 1D:
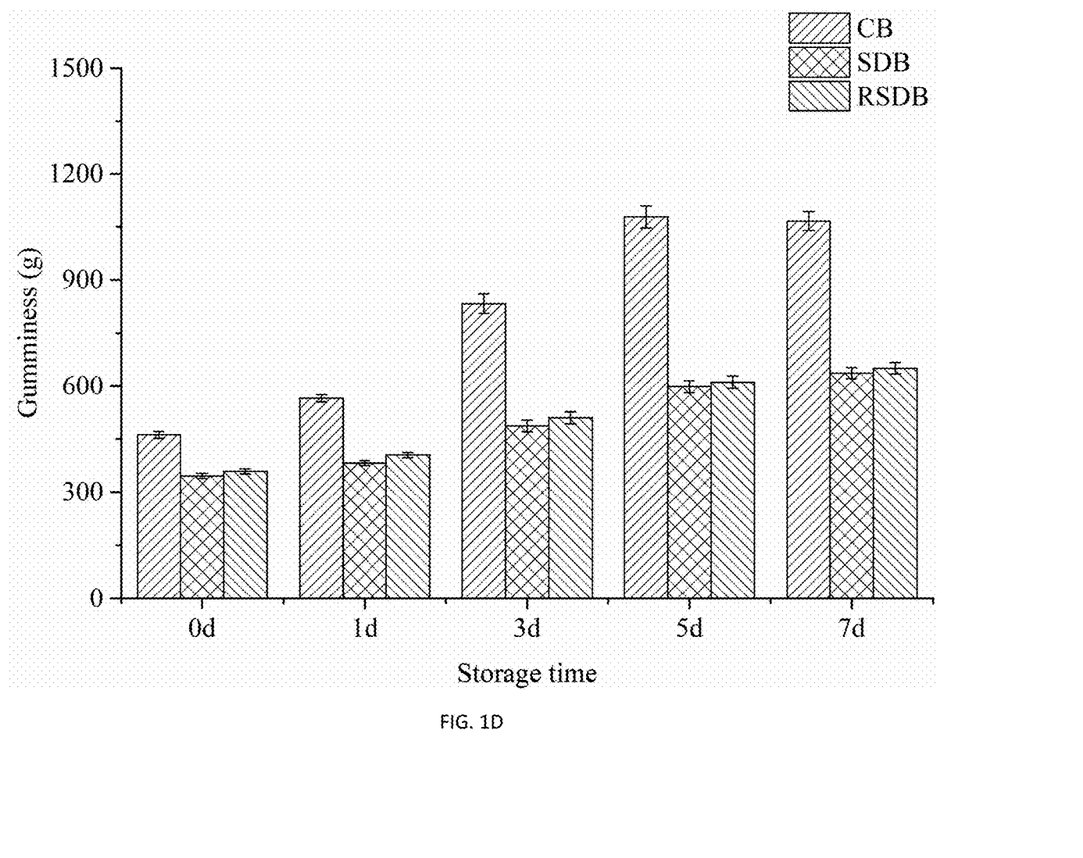
FIG. 1D shows Gumminess of bread made with different yeasts during storage (CB: commercial yeast bread, SDB: spontaneous sourdough bread, RSDB: compounded sourdough bread).
Figure 1E:
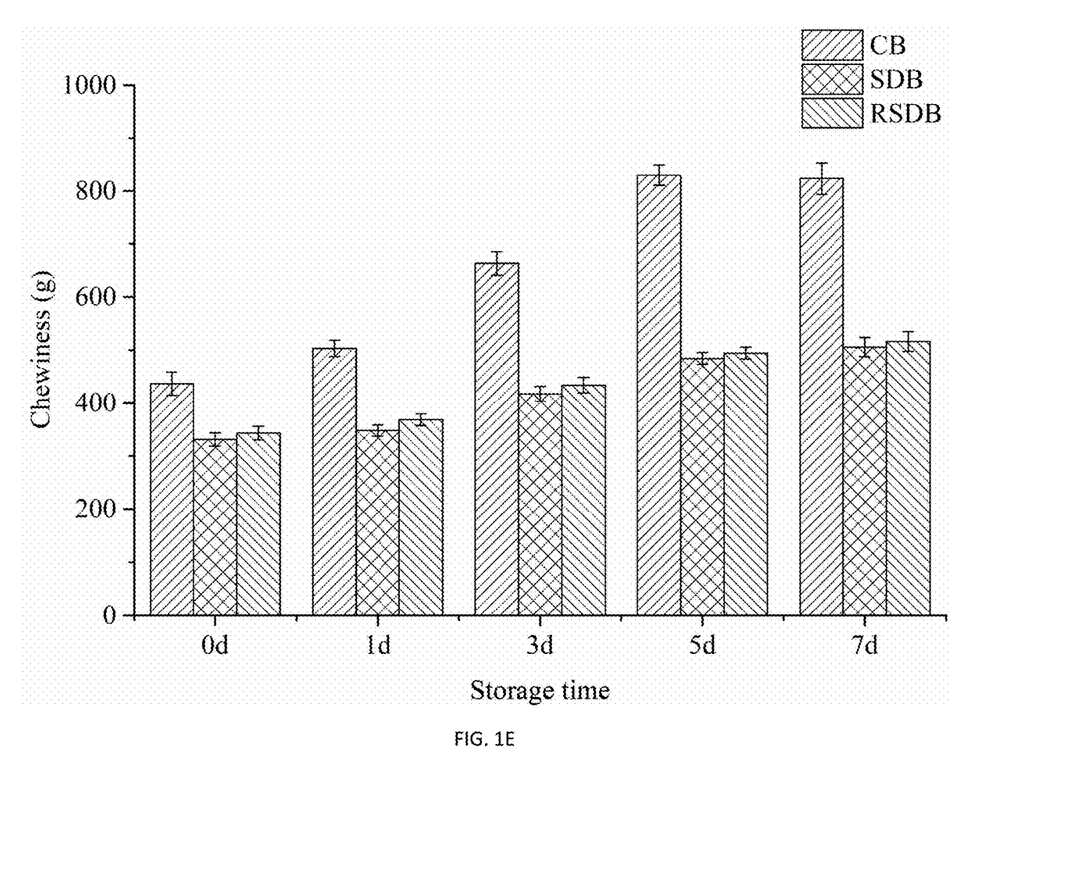
FIG. 1E shows Chewiness of bread made with different yeasts during storage (CB: commercial yeast bread, SDB: spontaneous sourdough bread, RSDB: compounded sourdough bread).
Figure 1F:
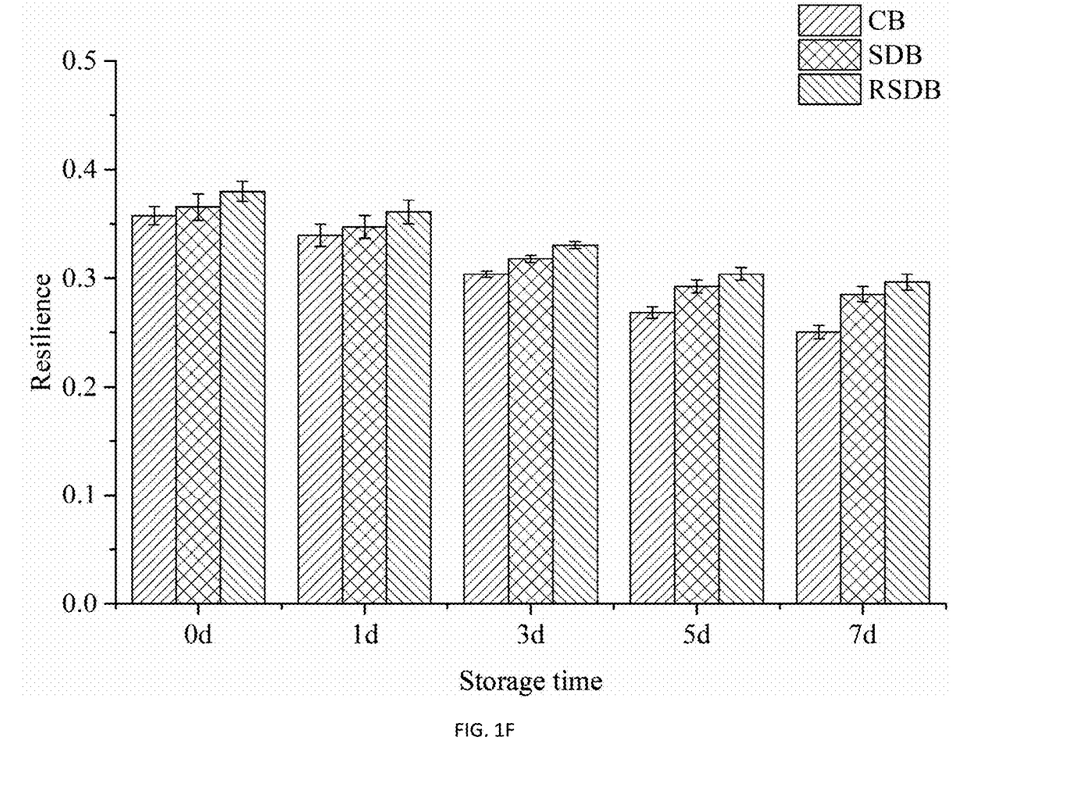
FIG. 1F shows Resilience of bread made with different yeasts during storage (CB: commercial yeast bread, SDB: spontaneous sourdough bread, RSDB: compounded sourdough bread).
Figure 2:
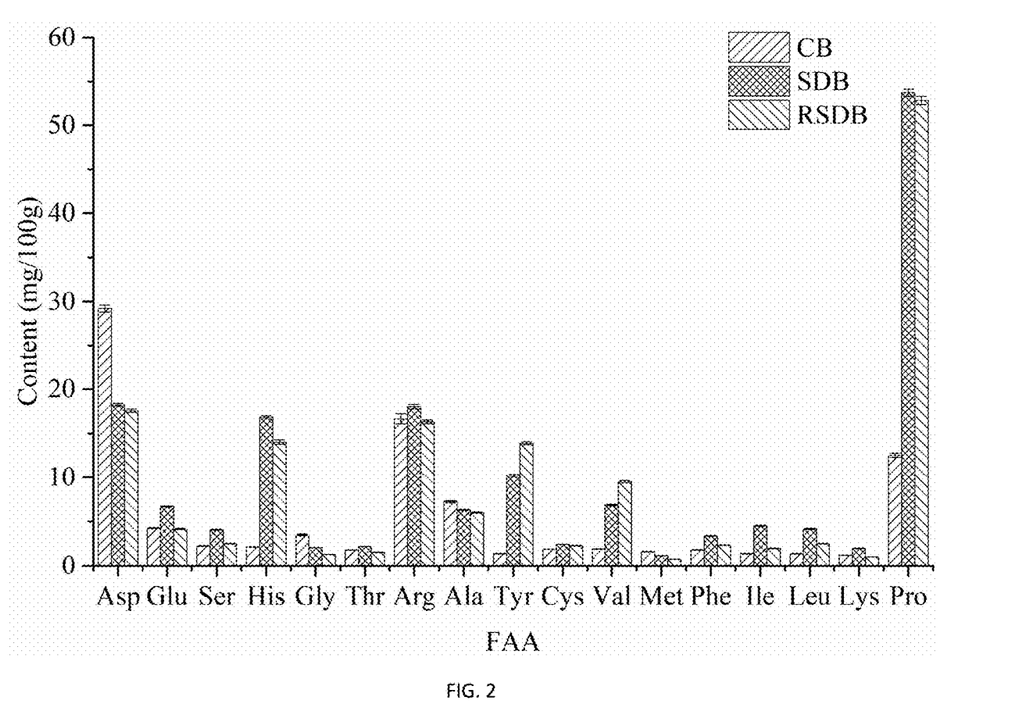
FIG. 2 shows the free amino acid content of bread made with different yeasts.

As can be seen from Table 5 and FIG. 2, the total amount of free amino acids in the compounded sourdough bread consistent with the present invention is significantly higher than that of commercial yeast bread, and is 1.5 times that of commercial yeast bread. Among them, the essential amino acid content of the compounded sourdough bread consistent with the present invention is about twice that of the commercial yeast bread. The use of compounded sourdough results in an increase in more than half of the free amino acid content. The quality of the compounded sourdough bread is similar to that of the spontaneous sourdough bread, and the compounded sourdough can be used to replace the spontaneous sourdough. The compounded sourdough bread is soft in texture, rich in flavor, good in taste, high in nutritional value and long in shelf life.

What is claimed is:

1. A method, comprising the following steps performed sequentially in the following order:
    a) expanding and culturing a bacterial solution consisting of *Lactobacillus brevis*, *Lactobacillus reuteri* and *Lactobacillus plantarum*, and collecting cells in a growth index period, wherein the *L. brevis*, *L. reuteri*, and *L. plantarum* are separately expanded and cultured in MRS or SDB medium;
    b) expanding and culturing *Saccharomyces cerevisiae* and collecting cells in a growth index period, wherein the *S. cerevisiae* are expanded and cultured in YPD medium;
    c) resuspending the cells of the *Saccharomyces cerevisiae*, the *Lactobacillus brevis*, the *Lactobacillus reuteri* and the *Lactobacillus plantarum* with sterile water, so that a concentration of each resuspended bacterial solution is $10^8$ to $10^{10}$ cells/mL; and
    d) compounding the resuspended bacterial solutions in a volume ratio, wherein the volume ratio of the resuspended bacterial solutions of the *Lactobacillus brevis* to the *Lactobacillus reuteri* to the *Lactobacillus plantarum* to the *Saccharomyces cerevisiae* is 4:4:4:1 to form a compounded bacterial suspension; and
    e) inoculating the compounded bacterial suspension into wheat flour dough at an inoculum amount of $10^7$ to $10^9$ viable cells in a compounded bacterial agent per gram of dough, and
    f) culturing the wheat flour dough at 20° C. to 28° C. for 8 to 15 hours to obtain a compounded sourdough.

2. The method according to claim 1, wherein the *L. brevis*, *L. reuteri*, and *L. plantarum* are inoculated into the MRS or SDB medium at an inoculum amount of 1% to 3%.

3. The method according to claim 1, wherein the *L. brevis*, *L. reuteri*, and *L. plantarum* are inoculated into the MRS or SDB medium at an inoculum amount of 1 to 3% and expanded and cultured at 26° C. to 30° C. or 35° C. to 39° C. for 8 to 14 hours, and wherein the cells in the growth index period are collected, centrifuged, collected, and then resuspended.

4. The method according to claim 2, wherein the *L. brevis*, *L. reuteri*, and *L. plantarum* are expanded and cultured at 26° C. to 30° C. or 35° C. to 39° C. for 8 to 14 hours, and wherein the cells in the growth index period are collected, centrifuged, collected and resuspended.

5. The method according to claim 1, wherein the *S. cerevisiae* are inoculated into the YPD medium at an inoculum amount of 1% to 3%.

6. The method according to claim 5, wherein the *S. cerevisiae* are expanded and cultured at 26° C. to 30° C. for 8 to 14 hours, and wherein the cells in the growth index period are collected, centrifuged, collected, and resuspended.

7. The method according to claim 4, wherein the *S. cerevisiae* are inoculated into the YPD medium at an inoculum amount of 1% to 3% and expanded and cultured at 26° C. to 30° C. for 8 to 14 hours, and wherein the cells in the growth index period are collected, centrifuged, collected, and resuspended.

8. A method, comprising the following steps performed sequentially in the following order:
    a) expanding and culturing a bacterial solution consisting of *Lactobacillus brevis*, *Lactobacillus reuteri* and *Lactobacillus plantarum*, collecting cells in a growth index period, wherein the *L. brevis*, *L. reuteri*, and *L. plantarum* are inoculated into the MRS or SDB medium at an inoculum amount of 1 to 3% and expanded and cultured at 26° C. to 30° C. or 35° C. to 39° C. for 8 to 14 hours, and wherein the cells in the growth index period are collected, centrifuged, collected, and then resuspended;

b) expanding and culturing *Saccharomyces cerevisiae* and collecting cells in a growth index period, wherein the *S. cerevisiae* are expanded and cultured in YPD medium, wherein the *S. cerevisiae* are expanded and cultured at 26° C. to 30° C. for 8 to 14 hours;

c) resuspending the cells of the *Saccharomyces cerevisiae*, the *Lactobacillus brevis*, the *Lactobacillus reuteri*, and the *Lactobacillus plantarum* with sterile water, so that a concentration of each resuspended bacterial solution is $10^8$ to $10^{10}$ cells/mL; and d) compounding the resuspended bacterial solutions in a volume ratio, wherein the volume ratio of the resuspended bacterial solutions of the *Lactobacillus brevis* to the *Lactobacillus reuteri* to the *Lactobacillus plantarum* to the *Saccharomyces cerevisiae* is 4:4:4:1 to form a compounded bacterial suspension; and e) inoculating the compounded bacterial suspension into wheat flour dough at an inoculum amount of $10^7$ to $10^9$ viable cells in a compounded bacterial agent per gram of dough, and f) culturing the wheat flour dough at 20° C. to 28° C. for 8 to 15 hours to obtain a compounded sourdough.

\* \* \* \* \*